United States Patent [19]

Little et al.

[11] 3,998,913
[45] Dec. 21, 1976

[54] FLAME RETARDANT SYSTEMS

[75] Inventors: Julian R. Little, Hendersonville, N.C.; Walter Nudenberg, West Caldwell, N.J.; Yong S. Rim, Waterbury, Conn.

[73] Assignee: Uniroyal, Inc., New York, N.Y.

[22] Filed: June 6, 1975

[21] Appl. No.: 584,513

Related U.S. Application Data

[60] Division of Ser. No. 445,885, Feb. 26, 1974, Pat. No. 3,932,525, which is a division of Ser. No. 347,455, April 3, 1973, Pat. No. 3,832,422, which is a continuation-in-part of Ser. No. 80,747, Oct. 10, 1970, abandoned.

[52] U.S. Cl. .................. 260/880 R; 260/2.5 AJ; 260/45.8 N; 260/45.9 NC; 260/45.95 C; 260/297 R; 260/561 R
[51] Int. Cl.$^2$ .................. C08K 5/20; C08K 5/34; C08K 5/41
[58] Field of Search .......... 260/45.8 N, 45.9 NC, 260/45.95 E, 297 R, 561 R, 880 R

[56] References Cited

UNITED STATES PATENTS

| | | | |
|---|---|---|---|
| 2,568,809 | 9/1951 | Kaiser | 260/619 |
| 2,775,591 | 12/1956 | Craig et al. | 260/247.7 |
| 3,843,598 | 10/1974 | Stach et al. | 260/45.75 |
| 3,850,943 | 11/1974 | Bowden et al. | 260/297 |
| 3,954,770 | 5/1976 | Mayerhoefer et al. | 260/268 |

*Primary Examiner*—Donald E. Czaja
*Assistant Examiner*—R. A. White
*Attorney, Agent, or Firm*—Hubbell, Cohen, Stiefel & Gross

[57] ABSTRACT

The known compound, 1,2,3,4,9,9-hexachloro-1,4-dihydro-1,4-methanonapthalene-5,8-diol (I) is an excellent flame retardant for ABS resins and polyurethanes, particularly, polyether-based polyurethanes. Compound (I) also forms novel molecular complexes with weak bases such as pyridine, pyridine HCl, pyridine oxide, dimethylsulfoxide and dimethylformamide, and which are excellent flame retardants for ABS resins. Compound (I) also exhibits unusual synergistic flame retardant effects in ABS resins and other polymers when used together with certain additives that are not themselves flame retardants.

10 Claims, No Drawings

FLAME RETARDANT SYSTEMS

CROSS REFERENCE TO RELATED APPLICATIONS

This is a division of application Ser. No. 445,885, filed Feb. 26, 1974, now U.S. Pat. No. 3,932,525, which is in turn a division of Ser. No. 347,455, filed Apr. 3, 1973, now U.S. Pat. No. 3,832,422, which is in turn a continuation-in-part of application Ser. No. 80,747, filed Oct. 10, 1970, now abandoned, the contents of all of said applications being expressly incorporated herein by reference.

BACKGROUND OF THE INVENTION

1. Field of the Invention

This invention relates to the field of flame retardants for polymers and to polymers rendered flame resistant therewith.

2. Description of the Prior Art

The increased use of polymeric materials, particularly in the building industry, has resulted in greatly increased interest in the fire retardancy of these materials. However, at the present time most commercially available plastics do not possess satisfactory fire retardancy and this inadequacy represents one of the major obstacles to the use of these materials.

Presently, the most widely used fire retardant chemicals are antimony trioxide and organohalogen compounds, the best known being chlorendic anhydride (1,4,5,6,7,7-hexachlorobicyclo[2.2.1]-hept-5-ene-2,3-dicarboxylic anhydride); tetrabromo- or tetrachlorophthalic acids; 1,4'-isopropylidenebis (2,6-dichlorophenol) [tetrachlorobisphenol A] or the corresponding bromine-containing compound; chloran i.e., 2,3-dicarboxyl-5,8-endomethylene-5,6,7,8,9,9-hexachloro-1,2,3,4,4a,5,8,8a-octahydronaphthalene anhydride; chlorinated parrafins; and dechlorane (dihexachlorocyclopentadiene).

The foregoing halogen compounds have only limited utility in polymer compositions due to a number of disadvantages. For example, when such halogen compounds are incorporated into a polymer, various physical properties of the polymer are modified, e.g., change in melt viscosity which requires higher processing temperatures, decrease in light stability, decrease in thermal stability, increase in density, adverse effects on heat distortion point, etc.

Some of these disadvantages have been overcome by the use of halogen-containing polymers as the flame retardant additive. Typical of such polymers are 2-chlorobutadiene, polyvinylchloride, chlorinated polyethylene and chlorosulfonated polyethylene. There are also, however, serious disadvantages associated with the use of such polymers. Among these are: (1) large amounts of halogen-containing polymers are required in order to obtain satisfactory fire retardancy due to the relatively low halogen content thereof; (2) the halogen-containing polymers have low thermal stabilities; and (3) the blending of the halogen-containing polymer with the polymer to be rendered flame retardant usually requires expensive processing techniques.

In addition, it is known from U.S. Pat. No. 3,678,116 that 1,2,3,4,9,9-hexachloro-1,4-dihydro-1,4-methanonaphthalene-5,8-diol (I) is useful as a flame retardant for polymer systems such as polyesters.

SUMMARY OF THE INVENTION

We have discovered a new system of chemical fire retardants for polymers such as acrylonitrile-butadiene-styrene (ABS) polymers and polyurethane polymers, hereinafter referred to as polyurethanes, and in particular, to polyether-based polyurethanes. The new system is based on the discovery that the known compound 1,2,3,4,9,9-hexachloro-1,4-dihydro-1,4-methanonaphthalene-5,8-diol (I) possesses unexpected and superior flame retardant properties with respect to ABS and polyurethanes. Thus, notwithstanding that compound (I) is known, from U.S. Pat. No. 3,678,116, to be effective in rendering polyesters flame retardant, we have now discovered that this compound is dramatically better in rendering ABS and polyurethanes flame resistant than it is in rendering polyesters flame retardant.

Accordingly, in one aspect thereof, the present invention provides a flame retardant composition comprising an ABS polymer or a polyurethane and an amount of compound (I) which is effective to render the polymer flame retardant. This effective amount varies somewhat depending on which polymer is being rendered flame retardant. Thus, when as little as about 6.0 parts of compound (I) are incorporated into 100 parts by weight of ABS, there is imparted to the ABS, considerable flame retardancy. With polyurethanes, on the other hand, as little as about 3.0 parts per hundred of compound (I) imparts good flame retardancy to the polyurethane, and with about 5.0 parts per hundred of compound (I), the flame retardancy of the polyurethane is outstanding. The invention also provides a method of rendering ABS and polyurethanes flame retardant by incorporating in the polymer an effective amount of compound (I).

We have also discovered that there is an unusual and unexpected synergistic effect exerted upon compound (I) by certain additives which are not themselves particularly effective as flame retardants and which do not synergize the effect of other known flame retardants including known polyhalogenated organic materials. In particular, these additives synergize the ability of compound (I) to impart flame retardancy to ABS polymers. Among these additives there are urea, magnesium oxide, magnesium sulfide, magnesium acetylacetonate, polyvinylchloride and other materials which generate stable free radicals, such as trityl chloride, $(C_6H_5)_3$—C—Cl and

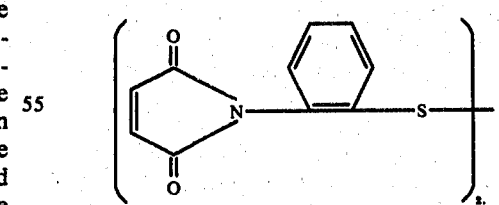

Accordingly, the present invention provides novel synergistic compositions for rendering ABS polymers flame retardant, these compositions comprising compound (I) and a synergizing amount of one of the above mentioned additives. This synergizing amount varies depending on the nature of the additive. Generally, about 1–5 parts of the additive added to the usual effective amount of compound (I), will, when incorporated in 100 parts of ABS, lead to a considerable improvement in the flame retardancy of the ABS compared to the use of compound (I) alone.

The preferred weight ratio of each of the above mentioned additives to compound (I) is given in the following Table I:

TABLE I

| Additive | Weight Ratio (Additive : Compound (I)) |
|---|---|
| urea | 3–6:10 |
| magnesium oxide | 1.4–4.4:7.7–10 |
| magnesium sulfide | 2.8:7.0 |
| magnesium acetylacetonate | 2.8:7.0 |
| polyvinylchloride | 15:6 |
| trityl chloride | 4.2:11.1 |
| 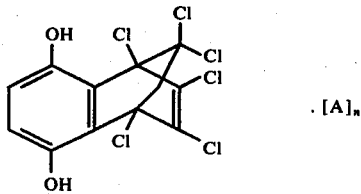 | 3–10:10 |

The present invention also provides novel flame retardant compositions comprising an ABS polymer and an effective amount of the above-described synergistic composition, as well as a method for rendering an ABS polymer flame retardant by incorporating into the ABS an effective amount of said synergistic composition.

We have also discovered, and the invention provides, a novel class of molecular complexes of compound (I) and weak bases such as pyridine, pyridine oxide, pyridinium hydrochloride, pyridinium methobromide, pyridinium methoiodide, dimethylsulfoxide and dimethylformamide.

These novel molecular complexes have the formula:

wherein A is pyridine, pyridine oxide, pyridinium hydrochloride, pyridinium methobromide, pyridinium methoiodide, dimethyl sulfoxide or dimethylformamide, and $n$ is 1 or 2.

The invention further provides flame retardant compositions comprising an ABS polymer and an effective amount of the above defined molecular complex. This effective amount will vary depending on which molecular complex is incorporated in the ABS polymer. Generally, it is at least about 4.0 parts per 100 parts by weight of the ABS polymer and preferably, between about 5 and 15 parts per 100 parts of the ABS polymer.

Finally, the invention provides a method of rendering an ABS polymer flame retardant by incorporating in the polymer an effective amount of the molecular complex.

The polymeric materials, i.e., ABS polymers and polyurethanes, are rendered flame retardant by incorporation of the flame retardant systems of the present invention into the polymer.

The flame retardant system may readily be incorporated into the polymeric material by a variety of methods depending on the nature of the polymer. Thus, for example, for those polymers which are adaptable to milling procedures and the like, the flame retardant system may simply be physically blended with the preformed polymer. With other types of polymers which require compounding, e.g., an uncured elastomer, or cannot readily be physically blended with other materials after formation of the polymer, the flame retardant system may be added to the compounding mixture of polymerization mixture.

DESCRIPTION OF THE PREFERRED EMBODIMENTS

In the following description and examples, reference will be made to ABS polymers and polyurethanes.

ABS (acrylonitrile-butadiene-styrene) polymers are members of the group known as gum plastics. These materials, also referred to as resin-rubber blends generally comprise a mixture of a hard, relatively brittle polymer (resin) and a minor portion of a relatively soft, rubbery polymer.

Suitable gum plastics which can be used in the present invention are described in U.S. Pat. No. 3,489,821, particularly column 1, line 52 — column 4, line 34 thereof, U.S. Pat. No. 3,489,822, particularly column 1, line 51 — column 4, line 45 thereof, said patents being incorporated by reference herein.

The ABS resins which best characterize the gum plastics, are made in a well known manner by interpolymerizing styrene and acrylonitrile monomers in the presence of a rubber which is either polybutadiene or a copolymer of butadiene and styrene, said copolymer containing not more than 10% by weight of combined styrene based on the sum of the weights of butadiene and styrene. Polymerization systems such as emulsion, mass, or solution are also applicable for ABS preparation. The manufacture of such ABS resins is shown in detail in U.S. Pat. Nos. 2,820,773, 2,802,809, 3,238,275 and 3,260,772, particularly column 3, lines 32–50 thereof, each of said patents being incorporated by reference herein. The ABS graft polymer-containing resins used in the present invention can be made with varying rubber content, this conveniently being achieved in accordance with known practice (e.g., as shown in U.S. Pat. No. 2,820,773) by admixing additional acrylonitrile-styrene copolymer latex of grafted material, and co-precipitating.

It is further possible to substitute for the acrylonitrile-styrene resinous portion, mixtures of styrene-acrylonitrile resin and a vinyl resin such as vinyl chloride polymer (particularly polyvinylchloride).

In place of using acrylonitrile itself for the preparation of the polymer, one may substitute for part or all of the acrylonitrile, equivalent similar monomers such as homologs or substitution products of acrylonitrile, e.g., methacrylonitrile and ethacrylonitrile.

Similarly, in place of using styrene itself in the preparation of the polymers used in the invention, one may substitute, for part or all of the styrene, equivalent monomers including substitution products of styrene, such as alkyl-substituted styrenes, including alpha-alkyl styrenes and nuclear alkyl-substituted styrenes such as alpha-methyl-styrene, other nuclear methyl-substituted styrenes, nuclear monoethyl-substituted styrenes, and mono- and di-chloro styrenes, etc.

Suitable polyurethanes are foamed and unfoamed rigid polyurethanes, i.e., organic diisocyanate-modified polyethers, polyesters, polyester-polyethers and polyester-polyamides, both saturated and olefinically unsaturated; and in particular, organic diisocyanate-modified polyethers. Such polymers are generally obtained from the reaction of a polyisocyanate, usually a diisocyanate, with a polyfunctional compound containing active-hydrogen groups, such as polyalkylene ether glycols, hydroxy-terminated polyesters, castor oil and polyester amides as well as mixtures of two or more of these classes of polyfunctional compounds. The material used for reaction with the polyisocyanate to make the polyurethane is frequently a polyether or polyester glycol having a molecular weight of from 400 to 6000, preferably in the 1000–2000 range. mention may be made of polyethers, such as polypropylene glycol, polypropylene-ethylene glycol and polytetramethylene glycol. Mention may also be made of chain extended polyesters made from a glycol (e.g., ethylene and/or propylene glycol) and a saturated dicarboxylic acid (e.g., adipic acid). Usually the starting glycol contains from 2 to 20 carbon atoms and the acid contains from 4 to 12 carbon atoms. Polyethylene adipate, polyethylene adipate-phthalate, polyneopentyl sebacate, etc. may be mentioned. Small amounts of tri-alcohols such as trimethylolpropane or trimethylolethane may be included. Among the suitable polyisocyantes may be mentioned m- and p-phenylene diisocyantes; toluene diisocyanate; p,p'-diphenylmethane diisocyanate; 3,3'-dimethyl (or dimethoxy)-4,4'-biphenyl diisocyanate; 1,5-naphthylene diisocyanate; p,p',p''-triphenylmethane triisocyanate; p-phenylene diisothiocyanate, etc. The isocyanate is, of course, used in an amount at least equivalent to the hydroxyl groups in the starting polymer; larger quantities of diisocyanate favor formation of liquid prepolymer. Generally, the molar ratio of diisocyanate to glycol is in the 1.2:1 to 3:1 range. For additional examples of suitable starting materials for making polyurethanes, reference may be had to the following: Otto Bayer in "Angewandte Chemie," A/59 (1947), No. 9, p. 264; and U.S. Pat. No. 3,105,062 incorporated herein by reference. Suitable polyurethanes are described in U.S. Pat. No. 3,412,071, particularly column 5, line 44 — column 4, line 6 thereof, U.S. Pat. Nos. 2,734,045 and 3,457,326, each of said patents being incorporated by reference herein.

The following examples illustrate the fire retardant effect of various amounts of compound (I) on an ABS polymer. The blends of compound (I) and the ABS polymer were prepared by mixing compound (I) and the ABS polymer in a conventional two roll mixing mill at 320° F. for 5 minutes. The compounded material was then molded to ⅛ inch thickness in a press. The molded sheets, after being cooled, were cut into strips and the strips were tested for fire retardance using the specified tests.

The test strips were evaluated for fire retardance using either ASTM method D-635, hereinafter referred to as "burn rate" and ASTM method D-2863, hereinafter referred to as "oxygen index". For the burn rate, the test strips were ⅛ × ½ × 5 inches, and for the oxygen index, the test strips were ⅛ × ¼ × 2½ inches.

The ABS gum plastic used was a gum plastic containing 22% acrylonitrile, 23% butadiene and 55% styrene.

The results of the fire retardance tests are set forth in Table II. (In the Tables, SE means self-extinguishing and NB means non-burning.)

TABLE II

| EXAMPLE | ABS PLASTIC (parts) | COMPOUND (I) (parts) | CHLORAN* (parts) | CHLORINE Content % Weight | BURN RATE Inches/Minutes | OXYGEN Index % |
|---|---|---|---|---|---|---|
| 1 | 100 | 0 | — | — | 1.80 | 18.3 |
| 2 | " | 6.0 | — | — | 1.60 | 23.2 |
| 3 | " | 8.7 | — | 4.5 | 1.11 | 24.0 |
| 4 | " | 11.6 | — | 5.8 | SE | 27.0 |
| 5 | " | 15.4 | — | 7.5 | SE | 28.0 |
| 6 | " | 25.0 | — | 11.2 | SE | 29.0 |
| 7 | " | — | 11.1 | 4.8 | 1.33 | 20.2 |
| 8 | " | — | 15.0 | 6.5 | 1.30 | 20.3 |
| 9 | " | — | 25.0 | 9.7 | 1.40 | 21.4 |

*a known commercial fire retardant

From the data, it can be seen that compound (I) is a much more effective flame retardant in ABS polymers than is chloran, a known flame retardant. Thus, when about 15 pph of compound (I) were added to ABS, the oxygen index increased from 18.3% (control) to 28.0%, an increase of 9.7%. When 15 pph of chloran were added to ABS. the oxygen index only increased from 18.3% (control) to 20.3%, an increase of 2.0%. Compound (I) is therefore 4.85 times more effective than chloran in making ABS flame retardant:

$$\frac{28.0 - 18.3}{20.3 - 18.3} = 4.85.$$

In the following Examples 10–19, the fire retardant effect of various amounts of compound (I) on a polyurethane were determined.

A series of samples were prepared by blending compound (I) and chloran with a thermoplastic polyether-based polyurethane (Roylar A-863; Uniroyal).

The samples were milled at 335° F. for 4 minutes and molded at 350° F. for 5 minutes.

The samples thus prepared were subjected to burn rate and oxygen index tests. The results of these tests are set out in Table III.

TABLE III

| EXAMPLE | POLYURETHANE (parts) | COMPOUND (I) (parts) | CHLORAN (parts) | DRIPPING | BURN RATE Inches/Minutes | OXYGEN Index % |
|---|---|---|---|---|---|---|
| 10 | 100 | 0 | — | XXX | 1.03 | 22.3 |
| 11 | " | 3 | — | XX | 0.53 | 23.3 |
| 12 | " | 5 | — | X | SE | 24.1 |
| 13 | " | 10 | — | None | SE | 25.4 |

TABLE III-continued

| EXAMPLE | POLYURETHANE (parts) | COMPOUND (I) (parts) | CHLORAN (parts) | DRIPPING | BURN RATE Inches/Minutes | OXYGEN Index % |
|---|---|---|---|---|---|---|
| 14 | " | 15 | — | None | NB | 31.3 |
| 15 | " | 25 | — | None | NB | 33.9 |
| 16 | " | — | 5 | XX | 0.60 | 23.1 |
| 17 | " | — | 10 | XX | 0.68 | 22.9 |
| 18 | " | — | 15 | XX | SE | 22.8 |
| 19 | " | — | 25 | X | SE | 22.5 |

XXX - heavy dripping
XX  - moderate dripping
X   - light dripping

One of the most serious problems encountered in the use of FR polyurethane elastoplastics for wire coatings is a dripping phenomena during combustion. Most inorganic flame retardants cannot be used for the polyurethane because of severe degradation of the physical properties thereof. As can be seen from the data in Table III, the use of compound (I) substantially diminishes the dripping and with 15 pph of compound (I), the polyurethane is rendered non-burning and non-dripping.

Compound (I) is a much more effective flame retardant than chloran as can be seen from the oxygen index test data in Table III. Thus, when 15 pph of compound (I) are added to the polyurethane, the oxygen index increased from 22.3% to 31.3%, an increase of 9.0%. When 15 pph of chloran were added to the polyurethane, the oxygen index only increased from 22.3% to 22.8%, an increase of 0.5%. Compound (I) is therefore 18 times more effective than chloran in making polyurethane flame retardant:

$$\frac{31.3 - 22.3}{22.8 - 22.3} = 18.0.$$

By way of comparison, the following Examples 20–25 illustrate the effects of compound (I) and chloran on two different polyesters.

TABLE IV

| EXAMPLE | POLYESTER (Parts) | | COMPOUND (I) (parts) | CHLORAN (parts) | OXYGEN Index % |
|---|---|---|---|---|---|
| | KODEL* | POLYTEX** | | | |
| 20 | 100 | — | 0 | 0 | 23.95 |
| 21 | 100 | — | 15 | 0 | 25.09 |
| 22 | 100 | — | 0 | 15 | 26.47 |
| 23 | — | 100 | 0 | 0 | 23.95 |
| 24 | — | 100 | 15 | 0 | 26.47 |
| 25 | — | 100 | 0 | 15 | 25.93 |

*Kodel - Eastman Kodak polyester
**Polytex - Industria Finishes Corp. polyester

As can be seen from the data in Table IV, compound (I) and chloran both have about the same effect in making two different polyesters flame retardant. However, as seen from the data in Tables II and III, compound (I) is much more effective than chloran in both ABS and polyurethanes. Thus, the discovery that compound (I) is so clearly superior in rendering ABS and polyurethanes flame retardant is quite an unexpected discovery.

The following examples illustrate the synergistic flame retardant effect between compound (I) and the additives described above when they are incorporated in an ABS polymer.

In Examples 26–31, varying amounts of compound (I) and the stable, free radical generating additives trityl chloride and

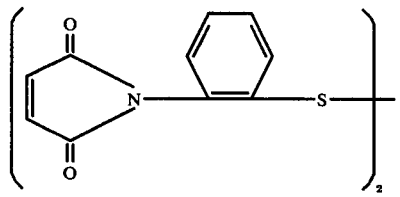

were incorporated in an ABS polymer and the oxygen indices were determined.

TABLE V

| EXAMPLE | ABS (parts) | COMPOUND (I) (parts) | ADDITIVE | PARTS | OXYGEN Index % |
|---|---|---|---|---|---|
| 26 | 100 | 10 | — | — | 27.7 |
| 27 | " | 10 | 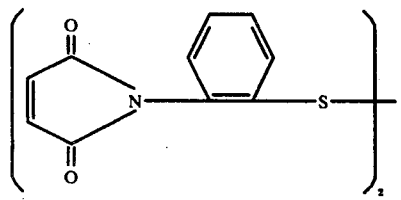 | 3 | 30.9 |
| 28 | " | 10 | | 5 | 30.2 |
| 29 | " | 10 | | 10 | 29.4 |
| 30 | " | 11.1 | trityl chloride | 4.2 | 32.4 |
| 31 | " | — | trityl chloride | 10 | 23.3 |

As can be seen from the data in Table V, both additives synergize the flame retardant effect of compound (I). The use of 3 parts per hundred of increases the oxygen index from 27.7% (compound (I) control) to 30.9%, an increase of 3.2%, while the use of 4.1 parts per hundred of trityl chloride increases the oxygen index even more, i.e., from 27.7% to 32.4%, an increase 4.7%.

The known flame retardants, chloran and chlorendic anhydride do not exhibit this synergism with the above additives.

In Examples 32–40, varying amounts of compound (I) and magnesium oxide, magnesium sulfide and magnesium acetylacetonate were incorporated in an ABS polymer and the flame retardant effects thereof were determined by both burn rate and oxygen index. The data are given below in Table VI.

TABLE VI

| EX-AM-PLE | ABS (parts) | COM-POUND (I) (parts) | MAG-NESIUM OXIDE (parts) | MAG-NESIUM SULFIDE (parts) | MAGNESIUM ACETYL-ACETONATE (parts) | BURN RATE Inches/ Minutes | OXY-GEN Index % |
|---|---|---|---|---|---|---|---|
| 32 | 100 | 7.7 | 0 | 0 | 0 | 1.48 | 24.06 |
| 33 | " | " | 1.4 | 0 | 0 | 0.98 | 24.13 |
| 34 | " | " | 2.8 | 0 | 0 | SE | 26.76 |
| 35 | " | " | 4.2 | 0 | 0 | SE | 27.25 |
| 36 | " | 10 | 0 | 0 | 0 | 1.51 | 26.96 |
| 37 | " | " | 3.0 | 0 | 0 | SE | 27.30 |
| 38 | " | " | 4.4 | 0 | 0 | NB | 27.63 |
| 39 | " | 7.0 | 0 | 2.8 | 0 | SE | 25.27 |
| 40 | " | " | 0 | 0 | 2.8 | SE | 25.68 |

As can be seen from the data in Table VI, magnesium oxide exerts a strong synergistic effect on compound (I) in ABS polymer. This effect is more clearly shown by the burn rate test than by the oxygen index although the latter also shows a considerable enhancement over the results obtained when compound (I) is used alone.

Thus, 7.7 parts of compound (I) per 100 of ABS showed an oxygen index of about 24.1 and burned relatively fast. However, the addition of 2.8 parts or more of magnesium oxide made the composition self-extinguishing and raised the oxygen index to about 27. When 3 or more parts of magnesium oxide were mixed with 10 parts of compound (I) in ABS the composition was made self-extinguishing or even non-burning, whereas the oxygen index was not raised appreciably above about 27.

Magnesium sulfide and magnesium acetylacetonate appear to be approximately as effective as magnesium oxide in increasing the fire retardant effect of compound (I).

This synergism is not exhibited by chloran or chlorendic anhydride.

In Examples 41–45, varying amounts of compound (I), chloran and urea were incorporated into an ABS polymer and the flame retardant effects thereof were determined by using both the burn rate and oxygen index tests. The data are set forth in Table VII.

TABLE VII

| EX-AM-PLE | ABS (parts) | ADDITIVES (parts) | | | BURN RATE Inches/ Minutes | OXY-GEN Index % |
|---|---|---|---|---|---|---|
| | | COM-POUND (I) | CHLO-RAN | UREA | | |
| 41 | 100 | 10 | — | — | 1.20 | 27.0 |
| 42 | " | — | 10 | — | 1.80 | 20.0 |
| 43 | " | 10 | — | 3 | SE | 33.3 |
| 44 | " | 10 | — | 6 | SE | 30.3 |
| 45 | " | — | 10 | 3 | 1.80 | 20.0 |

From the data in Table VII, it can be seen that the addition of 3 parts per hundred of urea together with 10 parts of compound (I) considerably improves the flame retardancy of an ABS polymer in comparison with the use of 10 parts of compound (I) alone. Thus, with 3 parts of urea, the polymer becomes self-extinguishing and the oxygen index increases from 27.0% to 33.3%.

This synergism is quite unexpected because urea alone is not a flame retardant and the addition of urea to chloran or chlorendic anhydride does not improve the flame retardancy thereof.

In Examples 46–50, varying amounts of compound (I), polyvinylchloride (PVC) and the known flame retardant, Dechloran 602 were incorporated into an ABS polymer and the flame retardant effects thereof were determined using both the burn rate and oxygen index tests. The data are set forth in Table VIII:

TABLE VIII

| EX-AM-PLE | ABS (parts) | ADDITIVES (parts) | | | BURN RATE Inches/ Minutes | OXY-GEN Index % |
|---|---|---|---|---|---|---|
| | | COM-POUND (I) | PVC | DECHLO-RAN 602 | | |
| 46 | 100 | 6 | 0 | 0 | 1.60 | 23.2 |
| 47 | " | 6 | 15 | 0 | SE | 27.5 |
| 48 | " | 0 | 15 | 0 | 1.70 | 19.3 |
| 49 | " | 0 | 0 | 15 | 1.60 | 20.4 |
| 50 | " | 0 | 15 | 7.7 | 1.50 | 20.6 |

The data in Table VIII show that the addition of 15 parts per hundred of PVC increases the oxygen index by 4.3% and makes the polymer composition self-extinguishing. In contrast, PVC alone or in combination with Dechloran 602 has no appreciable effect on either of the two criteria used to evaluate flame retardancy.

In the following Examples, the preparation of the novel molecular complexes of the invention will be described. In these Examples, all parts are by weight unless otherwise indicated.

EXAMPLE 51

Preparation of 1,2,3,4,9,9-hexachloro-1,4-dihydro-1,4-methanonaphthalene-5,8-diol 50 g. of 1,2,3,4,9,9-hexachloro-1,4,4a,8a-tetrahydro-1,4-methanonaphthalene-5,8-dione were dissolved in 300 ml. of methanol and 3 g. of pyridine were added. The mixture was refluxed until the yellow color disappeared (about 5 hours). Upon cooling to 5°–7° C., white crystals separated. One recrystallization from methanol gave white crystals, m.p. 186° C. The yield was almost quantitative.

The product has the following structure:

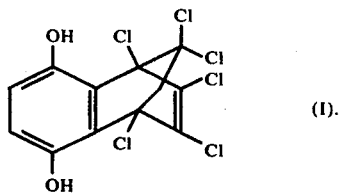

(I).

The dione starting material was prepared as follows:

A mixture of 54.6 g. (0.2 mole) of hexachlorocyclopentadiene, 21.6 g. (0.2 mole) of p-benzoquinone, and 10 ml. of toluene were placed in a 125 ml. round bottom flask and heated for 3 hours so that the toluene refluxed gently. At the end of this period the reaction mixture suddenly solidified completely, indicating completion of the reaction. The crude product was bright yellow. The damp material was transferred to a Buchner funnel, raised with absolute ethanol, dried on the funnel, and crystallized from ethanol. 49 g. of bright yellow dense crystals were obtained, m.p. 189°–193° C. (reported 188° C.). The yield was 64%.

The dione product has the following structure:

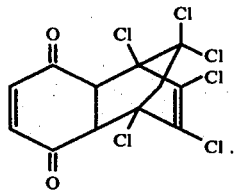

EXAMPLE 52

Preparation of molecular complex (1:1) of pyridine and 1,2,3,4,9,9-hexachloro-1,4-dihydro-1,4-methanonaphthalene-5,8-diol Pyridine (4.1 g., 0.0437 mole) was added to a solution of compound (I) prepared as in Example 51 (10.0 g., 0.0262 mole) in anhydrous ether (25 ml.). A white solid began to precipitate within one-half hour. The solid was separated and recrystallized from ether. Yield 9.0 g., 75%, m.p. 140°–142.5° C. The NMR spectrum and elemental analysis were consistent with the proposed structure.

Anal. calc'd. for $C_{16}H_9Cl_6NO_2$: C, 41.78; H, 1.97; Cl, 46.25; N, 3.05. Found: C, 41.94; H, 1.95; Cl, 46.63; N, 2.95.

The NMR spectrum showed 5 pyridine protons at 863 Hz, 783–741 Hz, 2 aromati protons at 736 Hz and 2 —OH protons at 667.5 Hz.

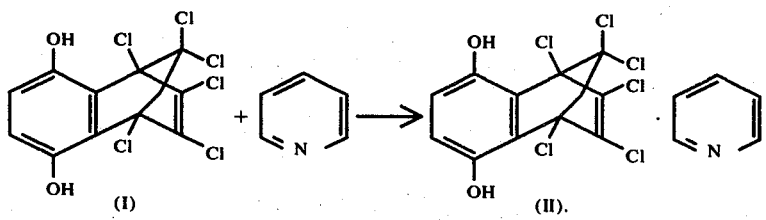

EXAMPLE 53

Preparation of molecular complex (1:2) of 1,2,3,4,9,9-hexachloro-1,4-dihydro-1,4-methanonaphthalene-5,8-diol and pyridinium hydrochloride A saturated ethereal hydrogen chloride solution was added to an ethereal solution of 1.0 gm. of the complex of Example 52 [compound (II)]. The white precipitate (0.8 g., m.p. 183°–6° C) was separated by filtration. This material was identical to the material obtained by reacting compound (I) with thionyl chloride and pyridine. The I.R. and elemental analysis were in agreement with the proposed structure.

Anal. calc'd. for $C_{21}H_{16}Cl_8N_2O_2$: C, 41.21; H, 2.64; Cl, 46.35; N, 4.58. Found: C, 40.47; H, 2.48; Cl, 45.72; N, 4.42.

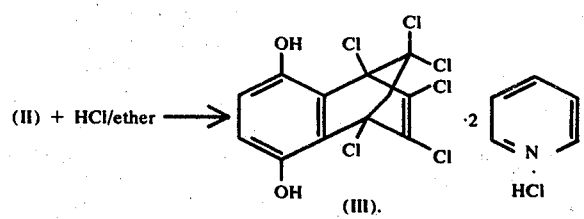

EXAMPLE 54

Preparation of molecular complex (2:1) of pyridinium methobromide and compound (I)

Methylbromide was bubbled through an ethereal solution of the complex of Example 52 [compound (II)] (15.0 g.) for 15 min. The flask was stoppered and allowed to stand at room temperature for 4 days. The resulting solid material was filtered to yield 3.6 g., m.p. 210°–212° C.

Anal. Calc'd. for $C_{23}H_{20}Cl_6Br_2N_2O_2$: C, 37.90; H, 2.77; Cl, 29.18; H, 3.84. Found: C, 37.57; H, 2.53; Cl, 29.91; N, 3.86.

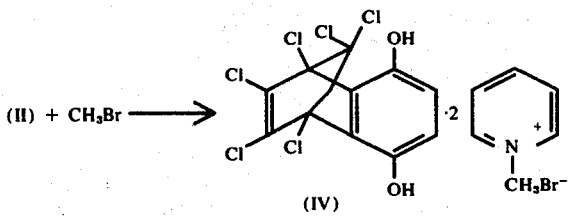

EXAMPLE 55

Preparation of molecular complex (2:1) of pyridinium methoiodide and compound (I)

This complex was prepared in a manner similar to that of Example 54 from 15 g. of compound (II) and 4.0 g. of methyliodide. The crude product (6.7 g.) was recrystallized from CHCl$_3$-ether to give a pure sample, m.p. 225° C.

Anal. Calc'd. for $C_{23}H_{20}Cl_6I_2N_2O_2$: C, 33.57; H, 2.45; Cl, 25.85; N, 3.40. Found: C, 33.47; H, 2.23; Cl, 26.90; N, 3.33.

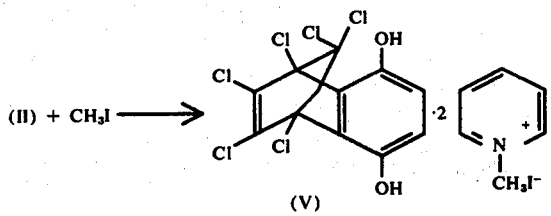

EXAMPLE 56

Preparation of the molecular complex of compound (I) and dimethylsulfoxide

Compound (I), 38 g. and an excess of dimethylsulfoxide (DMSO) were mixed in benzene and stirred for 20 minutes. The formed solid was recrystallized from benzene and white crystals were obtained, m.p. 160°–162° C. NMR, IR and elemental analysis were in good agreement with the proposed structure.

Anal. Calc'd. for $C_{13}H_{10}Cl_6O_3S$: C, 34.02; H, 2.20; Cl, 46.34; S, 6.99. Found: C, 33.80; H, 2.23; Cl, 46.42; S, 6.55.

The NMR spectrum showed 2 —OH protons at 729 Hz, 2 aromatic protons at 665 Hz and 6 DSMO protons at 262 Hz. Infrared analysis showed the presence of a —OH group at 3300 cm$^{-1}$ and a norbornene double bond at 1600 cm$^{-1}$.

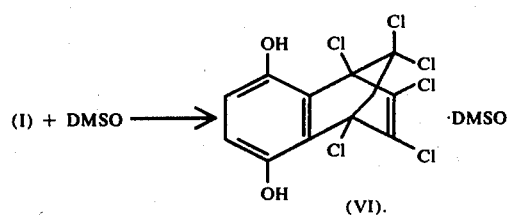

EXAMPLE 57

Preparation of the molecular complex of compound (I) and dimethylformamide (DMF)

This molecular complex was prepared by the same method as given in Example 56. The product melted at 110°–120° C.

Anal. Calc'd. for $C_{14}H_{10}Cl_6NO_3$: C, 37.04; H, 2.44; Cl, 46.86; N, 3.09. Found: C, 37.74; H, 2.69; Cl, 47.83; N, 3.13.

The NMR spectrum showed 2 aromatic protons at 670 Hz, 2 —OH protons at 636 Hz, and 2 methyl groups at 298 Hz and 292 Hz. Infrared analysis showed the presence of an —OH group at 3300 cm$^{-1}$ and a norbornene double bond at 1600 cm$^{-1}$.

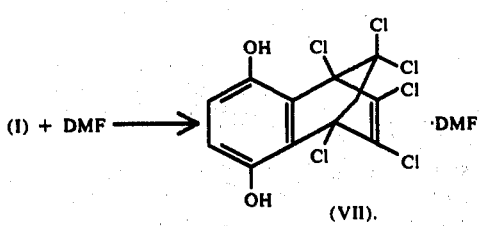

EXAMPLE 58

Preparation of the molecular complex (1:2) of compound (I) and pyridine oxide 19 g. of compound (I) and 10 g. of pyridine oxide were mixed in 150 ml. of anhydrous ether and stirred for 1 hour. The formed white solid was filtered off and recrystallized from benzene and white crystals were obtained, m.p. 146°–148° C. NMR, IR and elemental analysis agreed with the proposed structure.

Anal. Calc'd. for $C_{21}H_{16}Cl_6N_2O_2$: C, 44.04; H, 2.45; N, 4.91. Found: C, 43.87; H, 2.29; N, 4.71.

The NMR spectrum showed pyridine oxide protons at 832–819 Hz and 740–738 Hz, 2 aromatic protons at 671 Hz, and —OH protons at 819.5 Hz. Infrared analysis showed strong —OH group absorption at 3000–3300 cm$^{-1}$.

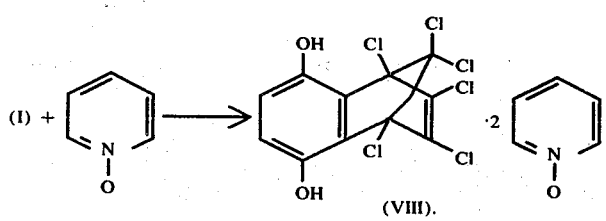

(VIII).

All of compounds VI, VII and VIII were stable even in hot water and were recrystallized easily from benzene.

In the following Examples 59–73, varying amounts of the molecular complexes prepared in Examples 52–58 were milled into an ABS resin and compression molded. The effectiveness of these complexes in rendering the ABS flame retardant was determined by the burn rate and oxygen index tests. The data are set forth in Table IX.

TABLE IX

| EXAMPLE | ABS (parts) | Additive, Compound No. | pph of Additive | BURN RATE Inches/Minutes | OXYGEN Index % |
|---|---|---|---|---|---|
| 59 | 100 | None | — | 1.80 | 18.5 |
| 60 | " | II | 10.0 | 1.28 | 27.3 |
| 61 | " | III | 4.0 | 1.78 | 29.3 |
| 62 | " | III | 5.8 | SE | 30.1 |
| 63 | " | III | 10.0 | NB | 35.6 |
| 64 | " | IV | 8.1 | — | 22.5 |
| 65 | " | V | 10.0 | 1.84 | 24.8 |
| 66 | " | VI | 10.0 | 1.20 | 27.0 |
| 67 | " | VI | 15.0 | SE | 28.0 |
| 68 | " | VII | 10.0 | 1.10 | 26.0 |
| 69 | " | VII | 15.0 | SE | 27.5 |
| 70 | " | VIII | 15.0 | SE | 28.0 |
| 71 | " | Chloran | 11.1 | 1.80 | 20.2 |
| 72 | " | Chloran | 20.0 | 1.75 | 21.4 |
| 73 | " | Chloran | 150 | SE | 29.8 |

The effectiveness of the molecular complexes of the invention as flame retardants is seen from the data in Table IX, wherein the complexes are compared with chloran.

As seen in Table IX, compound (II) at only a 5.8 parts per hundred level gives an oxygen index of 30.1 and a self-extinguishing composition, whereas it requires 150 parts per hundred of chloran to given an oxygen index of 29.8 and a self-extinguishing composition.

Thus, compound (II) is about 25 times better than chloran according to this test. Chloran at a 25 parts per hundred level gives an oxygen index of only 21.4.

Variations and modifications can, of course, be made without departing from the spirit and scope of the invention.

Having thus described our invention, what we desire to secure by Letters Patent and hereby claim is:

1. A flame retardant composition comprising an acrylonitrile-butadiene-styrene polymer and an effective amount of a molecular complex of the formula:

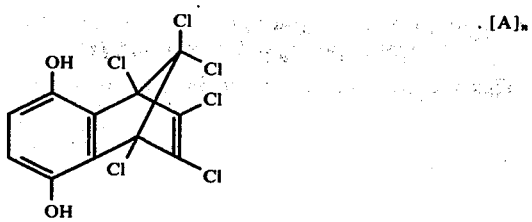

wherein A is pyridine, pyridine oxide, pyridinium hydrochloride, pyridinium methobromide, pyridinium methoiodide, dimethylsulfoxide or dimethylformamide and n is 1 or 2.

2. A flame retardant composition as claimed in claim 1, wherein the effective amount of said molecular complex is at least about 4.0 parts per 100 parts by weight of the acrylonitrile-butadiene-styrene polymer.

3. A flame retardant composition as claimed in claim 2, wherein the effective amount is about 5–15 parts per 100 parts of acrylonitrile-butadiene-styrene polymer.

4. A method for rendering an acrylonitrile-butadiene-styrene polymer flame retardant, said method comprising incorporating in the polymer an effective amount of a molecular complex of the formula:

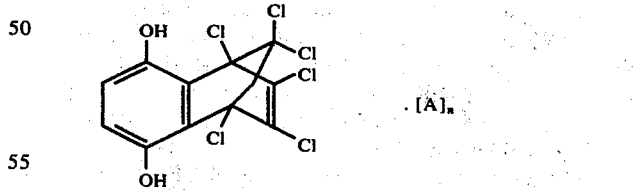

wherein A is pyridine, pyridine oxide, pyridinium hydrochloride, pyridinium methobromide, pyridinium methoiodide, dimethylsulfoxide or dimethylformamide and n is 1 or 2.

5. A method as claimed in claim 4, wherein the effective amount of said molecular complex is at least about 4.0 parts per 100 parts by weight of the acrylonitrile-butadiene-styrene polymer.

6. A method as claimed in claim 5, wherein the effective amount is about 5–15 parts per 100 parts of acrylonitrile-butadiene-styrene polymer.

7. A molecular complex of the formula:

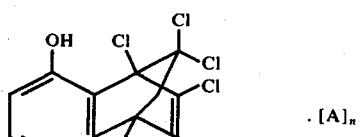

wherein A is pyridine, pyridine oxide, pyridinium hydrochloride, pyridinium methobromide, pyridinium methoiodide, or dimethylformamide and $n$ is 1 or 2.

8. A molecular complex as claimed in claim 7, wherein A is pyridine, or dimethylformamide and $n$ is 1.

9. A molecular complex as claimed in claim 7, wherein A is pyridine oxide, pyridinium hydrochloride, pyridinium methobromide or pyridinium methoiodide and $n$ is 2.

10. A molecular complex as claimed in claim 7, wherein A is dimethylformamide and $n$ is 1.

* * * * *

PO-1050
(5/69)

UNITED STATES PATENT OFFICE
CERTIFICATE OF CORRECTION

Patent No. 3,998,913  Dated December 21, 1976

Inventor(s) Julian R. Little et al

It is certified that error appears in the above-identified patent and that said Letters Patent are hereby corrected as shown below:

Column 1, line 39: "parrafins;" should read -- paraffins; --;

Column 3, line 2: "ABS compared" should read -- ABS as compared --;

Column 5, line 34: "range. mention" should read -- range. Mention --.

Column 12, line 11: "aromati" should read -- aromatic --.

Column 14, line 13: "6 DSMO" should read -- 6 DMSO --.

Signed and Sealed this

Eighth Day of March 1977

[SEAL]

Attest:

RUTH C. MASON
Attesting Officer

C. MARSHALL DANN
Commissioner of Patents and Trademarks